(12) United States Patent
Zhou et al.

(10) Patent No.: US 7,541,358 B2
(45) Date of Patent: Jun. 2, 2009

(54) 1-ARYL-OR 1-ALKYLSULFONYLBENZAZOLE DERIVATIVES AS 5-HYDROXYTRYPTAMINE-6 LIGANDS

(75) Inventors: Ping Zhou, Plainsboro, NJ (US); Michael Gerard Kelly, Thousand Oaks, CA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/891,961

(22) Filed: Aug. 14, 2007

(65) Prior Publication Data

US 2008/0027055 A1    Jan. 31, 2008

Related U.S. Application Data

(60) Division of application No. 10/888,810, filed on Jul. 9, 2004, now Pat. No. 7,271,180, which is a continuation-in-part of application No. 10/695,490, filed on Oct. 28, 2003, now abandoned, which is a division of application No. 10/314,726, filed on Dec. 9, 2002, now Pat. No. 6,710,069, which is a division of application No. 10/055,365, filed on Jan. 22, 2002, now Pat. No. 6,509,357.

(60) Provisional application No. 60/263,425, filed on Jan. 23, 2001.

(51) Int. Cl.
| | |
|---|---|
| A61K 31/5355 | (2006.01) |
| A61K 31/404 | (2006.01) |
| A61P 25/16 | (2006.01) |
| C07D 209/04 | (2006.01) |
| C07D 231/56 | (2006.01) |
| C07D 401/12 | (2006.01) |

(52) U.S. Cl. .............. 514/235.2; 514/322; 514/323; 514/406; 514/414; 514/415; 544/144; 546/201; 548/362.5; 548/465; 548/469; 548/503

(58) Field of Classification Search .................. None
See application file for complete search history.

(56) References Cited

U.S. PATENT DOCUMENTS

| | | | |
|---|---|---|---|
| 5,817,833 A | 10/1998 | Gaster | |
| 5,872,144 A | 2/1999 | Mewshaw | |
| 5,889,022 A | 3/1999 | Gaster et al. | |
| 6,127,380 A | 10/2000 | Nelson | |
| 6,255,494 B1 | 7/2001 | Britton et al. | |
| 6,322,770 B1 | 11/2001 | Rajopadhye et al. | |

FOREIGN PATENT DOCUMENTS

| | | |
|---|---|---|
| GB | 2341549 A | 3/2000 |
| WO | WO 97/31635 A1 | 9/1997 |
| WO | WO 98/30548 A1 | 7/1998 |
| WO | WO 00/46198 A1 | 8/2000 |
| WO | WO 02/14273 A1 | 2/2002 |

*Primary Examiner*—Kamal A Saeed
(74) *Attorney, Agent, or Firm*—Thomas C. McKenzie

(57) ABSTRACT

The present invention provides a compound of formula I and the use thereof for the therapeutic treatment of disorders relating to or affected by the 5-HT6 receptor.

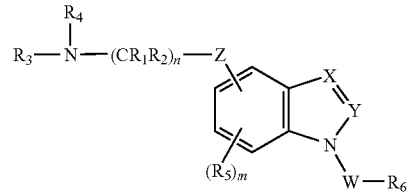

(I)

20 Claims, No Drawings

1-ARYL-OR 1-ALKYLSULFONYLBENZAZOLE DERIVATIVES AS 5-HYDROXYTRYPTAMINE-6 LIGANDS

BACKGROUND OF THE INVENTION

This Application is a divisional of application Ser. No. 10/888,810 filed on Jul. 9, 2004 now U.S. Pat. No. 7,271,180, which is a continuation-in-part of application Ser. No. 10/695,490 filed Oct. 28, 2003, now abandoned which in turn is a divisional of U.S. application Ser. No. 10/314,726, filed Dec. 09, 2002 now U.S. Pat. No. 6,710,069, which in turn is a divisional of U.S. application Ser. No. 10/055,365 filed Jan. 22, 2002 now U.S. Pat. No. 6,509,357, which in turn claims benefit under 35 U.S.C. § 119(e) of U.S. Provisional Application No. 60/263,425, filed Jan. 23, 2001, the entire disclosure of each Application is hereby incorporated by reference.

Various central nervous system disorders such as anxiety, depression, motor disorders, etc., are believed to involve a disturbance of the neurotransmitter 5-hydroxytryptamine (5-HT) or serotonin. Serotonin is localized in the central and peripheral nervous systems and is known to affect many types of conditions including psychiatric disorders, motor activity, feeding behavior, sexual activity, and neuroendocrine regulation among others. The effects of serotonin are regulated by the various 5-HT receptor subtypes. Known 5-HT receptors include the 5-HT1 family (e.g. 5-HT1A), the 5-HT2 family (e.g. 5-HT2A), 5-HT3, 5-HT4, 5-HT5, 5-HT6 and 5-HT7 subtypes.

The recently identified human 5-hydroxytryptamine-6 (5-HT6) receptor subtype has been cloned, and the extensive distribution of its mRNA has been reported. Highest levels of 5-HT6 receptor mRNA have been observed in the olfactory tubercle, the striatum, nucleus accumbens, dentate gyrus and CA1, CA2 and CA3 regions of the hippocampus. Lower levels of 5-HT6 receptor mRNA were seen in the granular layer of the cerebellum, several diencephalic nuclei, amygdala and in the cortex. Northern blots have revealed that 5-HT6 receptor mRNA appears to be exclusively present in the brain, with little evidence for its presence in peripheral tissues. The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Therefore, 5-HT6 receptor ligands are believed to be of potential use in the treatment of certain CNS disorders such as anxiety, depression, epilepsy, obsessive compulsive disorder, attention defecit disorders, migraine, cognitive memory enhancement (e.g. for the treatment of Alzheimer's disease), sleep disorders, feeding disorders (e.g. anorexia or bulimia), neurodegenerative disorders (e.g. head trauma or stroke),panic attacks, withdrawal from drug abuse (e.g. cocaine, ethanol, nicotine or benzodiazepines), schizophrenia, or the like; or in the treatment of certain gastrointestinal disorders such as irritable bowel syndrome.

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

It is a feature of this invention that the compounds provided may also be used to further study and elucidate the 5-HT6 receptor.

These and other objects and features of the invention will become more apparent by the detailed description set forth hereinbelow.

SUMMARY OF THE INVENTION

The present invention provides a compound of formula I

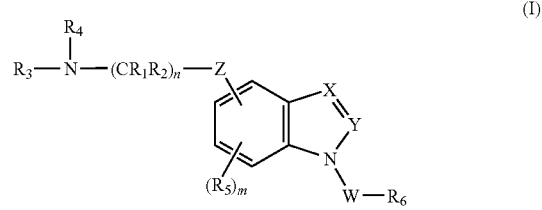

wherein
W is $SO_2$, CO, CONH, CSNH or $CH_2$;
X is $CR_7$ or N;
Y is $CR_8$ or N with the proviso that when X is N, then Y must be $CR_8$;
Z is O, $SO_p$ or $NR_9$;
$R_1$ and $R_2$ are each independently H or $C_1$-$C_6$alkyl;
n is an integer of 2, 3 or 4;
$R_3$ and $R_4$ are each independently H, $CNR_{10}NR_{11}R_{12}$ or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_3$ and $R_4$ may be taken together with the atom to which they are attached to form an optionally substituted 3- to 6-membered ring optionally containing an additional heteroatom selected from O, N or S;
$R_5$ is H, halogen, CN, $OR_{13}$, $CO_2R_{14}$, $CONR_{15}R_{16}$, $CNR_{17}NR_{18}R_{19}$, $SO_2NR_{20}R_{21}$, $SO_qR_{22}$ or a $C_1$-$C_6$alkyl, $C_2$-$C_6$alkenyl, $C_2$-$C_6$alkynyl, $C_3$-$C_6$cycloalkyl, cycloheteroalkyl, phenyl or heteroaryl group each optionally substituted;
m is an integer of 1, 2 or 3;
p and q are each independently 0 or an integer of 1 or 2;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
$R_7$ and $R_8$ are each independently H, halogen or a $C_1$-$C_6$ alkyl, aryl, heteroaryl or $C_1$-$C_6$alkoxy group each optionally substituted;
$R_9$ is H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{10}$, $R_{11}$, $R_{12}$, $R_{15}$, $R_{16}$, $R_{17}$, $R_{18}$ and $R_{19}$ are each independently H or $C_1$-$C_4$alkyl;
$R_{13}$ is H, $COR_{23}$ or a $C_1$-$C_6$alkyl, $C_2$-$C_6$alkenyl, $C_2$-$C_6$alkynyl, aryl or heteroaryl group each optionally substituted;
$R_{14}$ is H or a $C_1$-$C_6$alkyl, aryl or heteroaryl group each optionally substituted;
$R_{20}$ and $R_{21}$ are each independently H or a $C_1$-$C_6$alkyl, aryl or heteroaryl group each optionally substituted; and
$R_{22}$ and $R_{23}$ are each independently an optionally substituted $C_1$-$C_6$alkyl, aryl or heteroaryl group; or a pharmaceutically acceptable salt thereof.

The present invention also provides methods and compositions useful for the therapeutic treatment of central nervous system disorders related to or affected by the 5-HT6 receptor.

DETAILED DESCRIPTION OF THE INVENTION

The 5-hydroxytryptamine-6 (5-HT6) receptor is one of the most recent receptors to be identified by molecular cloning. Its ability to bind a wide range of therapeutic compounds used in psychiatry, coupled with its intriguing distribution in the brain has stimulated significant interest in new compounds which are capable of interacting with or affecting said receptor. At present, there are no known fully selective agonists. Significant efforts are being made to understand the possible role of the 5-HT6 receptor in psychiatry, cognitive dysfunction, motor function and control, memory, mood and the like. To that end, compounds which demonstrate a binding affinity for the 5-HT6 receptor are earnestly sought both as an aid in the study of the 5-HT6 receptor and as potential therapeutic agents in the treatment of central nervous system disorders.

Surprisingly, it has now been found that 1-aryl- or 1-alkyl-sulfonylbenzazole derivatives of formula I demonstrate 5-HT6 affinity. Advantageously, said benzazole derivatives may be used as effective therapeutic agents for the treatment of central nervous system (CNS) disorders associated with or affected by the 5-HT6 receptor. Accordingly, the present invention provides 1-alkyl- or 1-arylsulfonylbenzazole derivatives of formula I

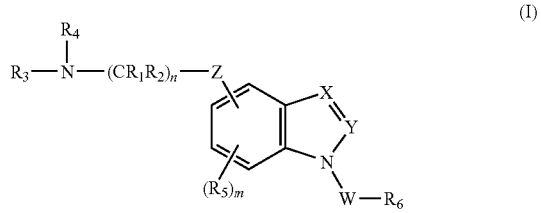

(I)

wherein
W is $SO_2$, CO, CONH, CSNH or $CH_2$;
X is $CR_7$ or N;
Y is $CR_8$ or N with the proviso that when X is N, then Y must be $CR_8$;
Z is O, $SO_p$ or $NR_9$;
$R_1$ and $R_2$ are each independently H or $C_1$-$C_6$alkyl;
n is an integer of 2, 3 or 4;
$R_3$ and $R_4$ are each independently H, $CNR_{10}NR_{11}R_{12}$, or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted, or $R_3$ and $R_4$ may be taken together with the atom to which they are attached to form an optionally substituted 3- to 6-membered ring optionally containing an additional heteroatom selected from O, N or S;
$R_5$ is H, halogen, CN, $OR_{13}$, $CO_2R_{14}$, $CONR_{15}R_{16}$, $CNR_{17}NR_{18}R_{19}$, $SO_2NR_{20}R_{21}$, $SO_qR_{22}$ or a $C_1$-$C_6$alkyl, $C_2$-$C_6$alkenyl, $C_2$-$C_6$alkynyl, $C_3$-$C_6$cycloalkyl, cycloheteroalkyl, phenyl or heteroaryl group each optionally substituted;
m is an integer of 1, 2 or 3;
p and q are each independently 0 or an integer of 1 or 2;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
$R_7$ and R8 are each independently H, halogen or a $C_1$-$C_6$alkyl, aryl, heteroaryl or $C_1$-$C_6$alkoxy group each optionally substituted;
$R_9$ is H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{10}$, $R_{11}$, $R_{12}$, $R_{15}$, $R_{16}$, $R_{17}$, $R_{18}$ and $R_{19}$ are each independently H or $C_1$-$C_4$alkyl;
$R_{13}$ is H, $COR_{23}$ or a $C_1$-$C_6$alkyl, $C_2$-$C_6$alkenyl, $C_2$-$C_6$alkynyl, aryl or heteroaryl group each optionally substituted;
$R_{14}$ is H or a $C_1$-$C_6$alkyl, aryl or heteroaryl group each optionally substituted;
$R_{20}$ and $R_{21}$ are each independently H or a $C_1$-$C_6$alkyl, aryl or heteroaryl group each optionally substituted; and
$R_{22}$ and $R_{23}$ are each independently an optionally substituted $C_1$-$C_6$alkyl, aryl or heteroaryl group; or a pharmaceutically acceptable salt thereof.

As used in the specification and claims, the term halogen designates Br, Cl, I or F and the term cycloheteroalkyl designates a $C_5$-$C_7$cycloalkyl ring system containing 1 or 2 heteroatoms, which may be the same or different, selected from N, O or S and optionally containing one double bond. Exemplary of the cycloheteroalkyl ring systems included in the term as designated herein are the following rings wherein Q is NR, O or S; and R is H or an optional substituent as defined hereinbelow.

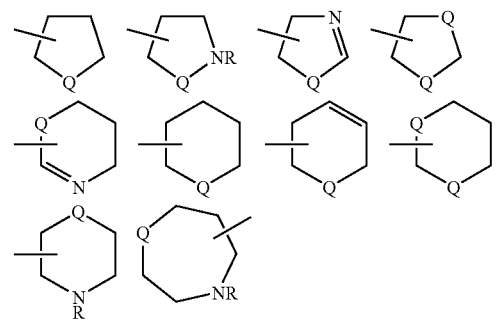

Similarly, as used in the specification and claims, the term heteroaryl designates a $C_5$-$C_{10}$ aromatic ring system containing 1 or 2 heteroatoms, which may be the same or different, selected from N, O or S. Such heteroaryl ring systems include pyrrolyl, azolyl, oxazolyl, thiazolyl, imidazolyl, furyl, thienyl, pyridyl, quinolinyl, isoquinolinyl, indolinyl, benzothienyl, benzofuranyl, benzisoxazolyl and the like; the term haloalkyl designates a $C_nH_{2n+1}$ group having from one to 2n+1 halogen atoms which may be the same or different; and the term haloalkoxy designates an $OC_nH_{2n+1}$ group having from one to 2n+1 halogen atoms which may be the same or different.

Exemplary of the 8- to 13-membered bicyclic or tricyclic ring systems having a N atom at a bridgehead and optionally containing 1, 2 or 3 additional heteroatoms selected from N, O or S included in the term as designated herein are the following ring systems wherein W is NR, O or S; and R is H or an optional substituent as described hereinbelow:

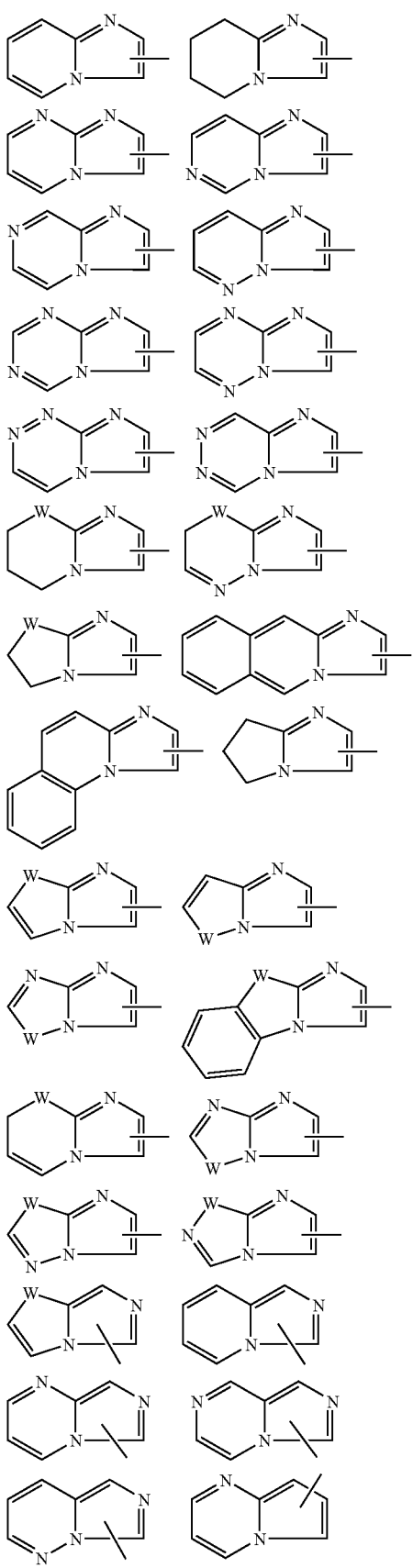

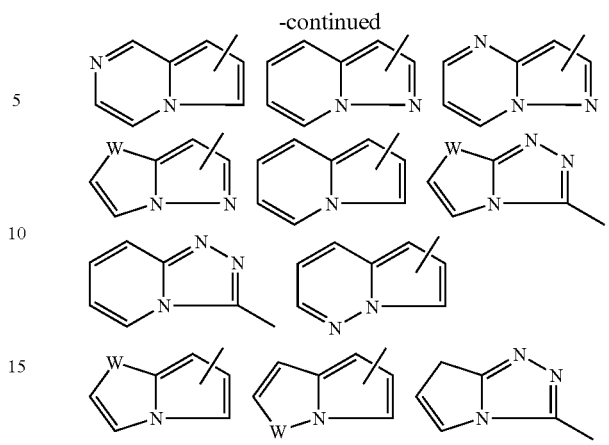

In the specification and claims, when the terms $C_1$-$C_6$alkyl, $C_2$-$C_6$alkenyl, $C_2$-$C_6$alkynl, $C_3$-$C_7$cycloalkyl, cycloheteroalkyl, aryl, heteroaryl or 8- to 13-membered bicyclic or tricyclic ring system having a N atom at the bridgehead are designated as being optionally substituted, the substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl groups. Typically, 0-3 substituents may be present. When any of the foregoing substituents represents or contains an alkyl substituent group, this may be linear or branched and may contain up to 12, preferably up to 6, more preferably up to 4 carbon atoms.

Pharmaceutically acceptable salts may be any acid addition salt formed by a compound of formula I and a pharmaceutically acceptable acid such as phosphoric, sulfuric, hydrochloric, hydrobromic, citric, maleic, malonic, mandelic, succinic, fumaric, acetic, lactic, nitric, sulfonic, p-toluene sulfonic, methane sulfonic acid or the like.

Preferred compounds of the invention are those compounds of formula I wherein W is $SO_2$ or CO. Also preferred are those compounds of formula I wherein Z is O. Another group of preferred compounds of the invention are those compounds of formula I wherein n is 2.

More preferred compounds of the invention are those compounds of formula I wherein W is $SO_2$; $R_1$ and $R_2$ are H; and n is 2. Another group of more preferred compounds of the invention are those compounds of formula I wherein W is $SO_2$; Z is O; X is $CR_7$; and $R_3$ and $R_4$ are taken together with the atom to which they are attached to form a 5- or 6-membered ring optionally containing one oxygen atom.

Among the preferred compounds of the invention are:
1-[(5-chlorothien-2-yl)sulfonyl]-5-[2-(piperidin-1-yl)ethoxy]-1H-indole;
1-[(4,5-dichlorothien-2-yl)sulfonyl]-5-[2-(piperidin-1-yl)ethoxy]-1H-indole;
1-[(6-chloroimidazo[2,1-b][1,3]thiazol-5-yl)sulfonyl]-5-[2-(piperidin-1-yl)ethoxy]-1H-indole;
1-[(5-chloro-3-methyl-1-benzothien-2-yl)sulfonyl]-5-[2-(piperidin-1-yl)ethoxy]-1H-indole;

1-[(5-chloro-3-methyl-1-benzothien-2-yl)sulfonyl]-4-[2-(piperidin-1-yl)ethoxy]-1H-indole;
1-[(6-chloroimidazo[2,1-b][1,3]thiazol-5-yl)sulfonyl]-4-[2-(piperidin-1-yl)ethoxy]-1H-indazole;
1-[(4,5-dichlorothien-2-yl )sulfonyl]-4-[2-(piperidin-1-yl)ethoxy]-1H-indazole;
1-[(5-chlorothien-2-yl)sulfonyl]-4-[2-(piperidin-1-yl)ethoxy]-1H-indazole;
4-[2-(piperidin-1-yl)ethoxy]-1-(thien-2-ylsulfonyl)-1H-indazole;
1-[(5-chloro-3-methyl-1-benzothien-2-yl)sulfonyl]-4-[2-(piperidin-1-yl)ethoxy]-1H-indazole; or a pharmaceutically acceptable salt thereof.

Compounds of the invention may be prepared using conventional synthetic methods and, if required, standard separation and isolation techniques. For example, compounds of formula I wherein W is $SO_2$, $R_1$ and $R_2$ are H, and Z is O may be prepared by reacting an hydroxybenzazole intermediate of formula II with a haloalkanol of formula III in the presence of triphenylphosphine and diethyl azodicarboxylate to give the haloalkoxy derivative of formula IV; sulfonating the formula IV derivative to give the 1-sulfonylbenzazole compound of formula V; and displacing the halo group of said formula V compound with the appropriate amine to give the desired compounds of formula Ia. The reaction sequence is illustrated in flow diagram I wherein Hal designates a halogen atom.

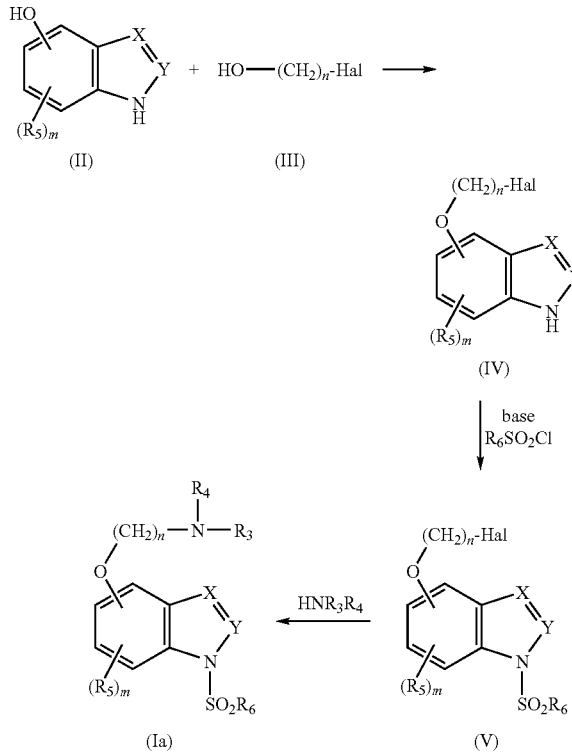

FLOW DIAGRAM I

Alternatively, compounds of formula Ia may be prepared by reacting the intermediate of formula V with $NaN_3$ to form the corresponding benzazolyloxyalkylazide of formula VI; reducing said formula VI azide with triphenylphosphine to give the formula I compound wherein Z is O and $R_1$, $R_2$, $R_3$ and $R_4$ are H(Ib); and optionally alkylating said formula Ib compound to give compounds of formula Ia. The reactions are illustrated in flow diagram II.

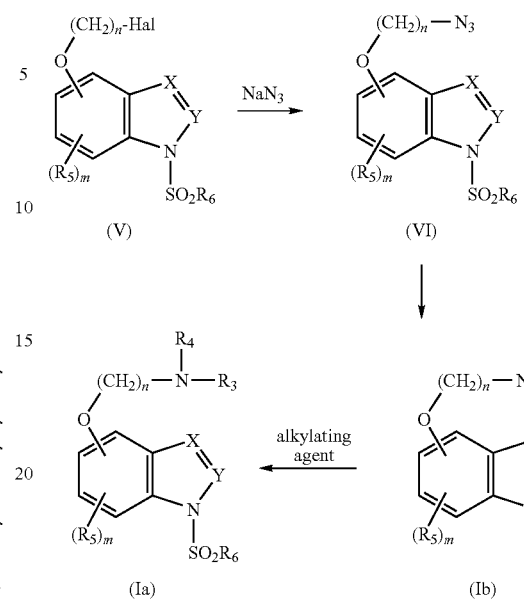

FLOW DIAGRAM II

Similarly, compounds of formula I wherein W is $SO_2$ and Z is S may be prepared by utilizing the appropriate benzazolylthiol starting material and employing essentially the same reaction sequences shown hereinabove in flow diagrams I and II.

Compounds of formula I wherein W is $SO_2$ and Z is NH (Ic) may be prepared by sulfonating a nitrobenzazole intermediate of formula VII to give the corresponding 1-sulfonyl derivative of formula VIII; reducing the formula VIII compound to give the corresponding amine of formula IX; reacting said amine with a haloalkylaldehyde of formula X to give the haloalkylamine derivative of formula XI; and displacing the halo group of said formula XI derivative with the appropriate amine to give the desired compounds of formula Ic. The reaction sequence is shown in flow diagram III.

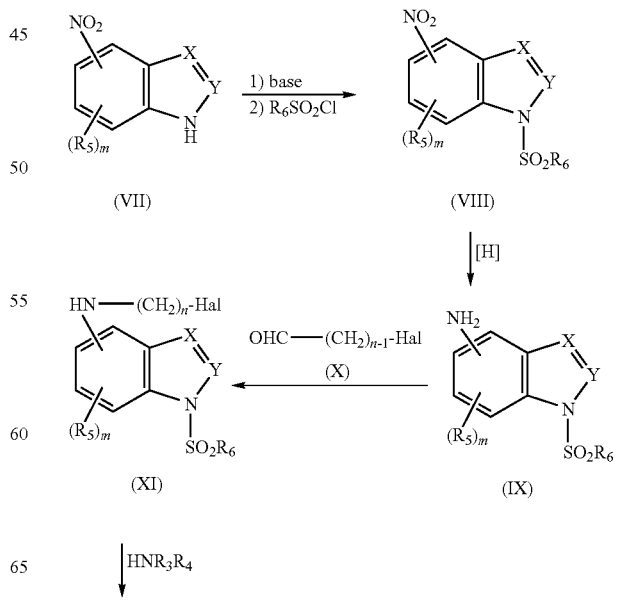

FLOW DIAGRAM III

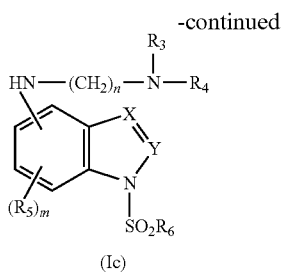

(Ic)

Compounds of formula I wherein W is CO and Z is O may be prepared by reacting a compound of formula IV with the appropriate isocyanate or carbonyl or carbamoyl halide in the presence of a base. Using these and other conventional methods, compounds of formula I may be prepared from readily available starting materials.

Advantageously, the inventive compound of formula I may be utilized in the treatment of central nervous system disorders relating to or affected by the 5-HT6 receptor such as motor, mood, psychiatric, cognitive, neurodegenerative, or the like disorders. Accordingly, the present invention provides a method for the treatment of a disorder of the central nervous system (CNS) related to or affected by the 5-HT6 receptor in a patient in need thereof which comprises providing said patient a therapeutically effective amount of a compound of formula I as described hereinabove. The compounds may be provided by oral or parenteral administration or in any common manner known to be an effective administration of a therapeutic agent to a patient in need thereof.

The therapeutically effective amount provided in the treatment of a specific CNS disorder may vary according to the specific condition(s) being treated, the size, age and response pattern of the patient, the severity of the disorder, the judgment of the attending physician and the like. In general, effective amounts for daily oral administration may be about 0.01 to 1,000 mg/kg, preferably about 0.5 to 500 mg/kg and effective amounts for parenteral administration may be about 0.1 to 100 mg/kg, preferably about 0.5 to 50 mg/kg.

In actual practice, the compounds of the invention are provided by administering the compound or a precursor thereof in a solid or liquid form, either neat or in combination with one or more conventional pharmaceutical carriers or excipients. Accordingly, the present invention provides a pharmaceutical composition which comprises a pharmaceutically acceptable carrier and an effective amount of a compound of formula I as described hereinabove.

Solid carriers suitable for use in the composition of the invention include one or more substances which may also act as flavoring agents, lubricants, solubilizers, suspending agents, fillers, glidants, compression aides, binders, tablet-disintegrating agents or encapsulating materials. In powders, the carrier may be a finely divided solid which is in admixture with a finely divided compound of formula I. In tablets, the formula I compound may be mixed with a carrier having the necessary compression properties in suitable proportions and compacted in the shape and size desired. Said powders and tablets may contain up to 99% by weight of the formula I compound. Solid carriers suitable for use in the composition of the invention include calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Any pharmaceutically acceptable liquid carrier suitable for preparing solutions, suspensions, emulsions, syrups and elixirs may be employed in the composition of the invention. Compounds of formula I may be dissolved or suspended in a pharmaceutically acceptable liquid carrier such as water, an organic solvent, or a pharmaceutically acceptable oil or fat, or a mixture thereof. Said liquid composition may contain other suitable pharmaceutical additives such as solubilizers, emulsifiers, buffers, preservatives, sweeteners, flavoring agents, suspending agents, thickening agents, coloring agents, viscosity regulators, stabilizers, osmo-regulators, or the like. Examples of liquid carriers suitable for oral and parenteral administration include water (particularly containing additives as above, e.g., cellulose derivatives, preferably sodium carboxymethyl cellulose solution), alcohols (including monohydric alcohols and polyhydric alcohols, e.g., glycols) or their derivatives, or oils (e.g., fractionated coconut oil and arachis oil). For parenteral administration the carrier may also be an oily ester such as ethyl oleate or isopropyl myristate.

Compositions of the invention which are sterile solutions or suspensions are suitable for intramuscular, intraperitoneal or subcutaneous injection. Sterile solutions may also be administered intravenously. Inventive compositions suitable for oral administration may be in either liquid or solid composition form.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms HPLC and NMR designate high performance liquid chromatography and nuclear magnetic resonance, respectively. The terms EtOAc and $Et_2O$ designate ethyl acetate and diethyl ether, respectively.

EXAMPLE 1

Preparation of 4-(2-Chloroethoxy)-1H-Indole

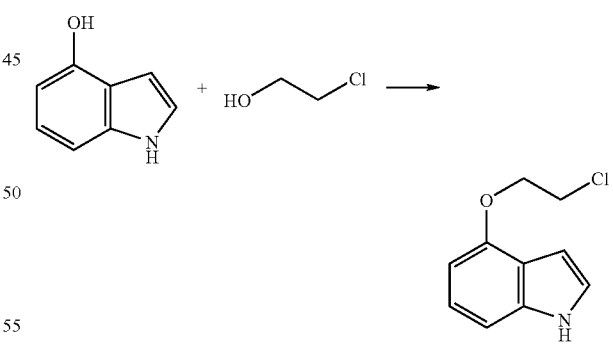

A solution of 4-hydroxyindole (3.99 g, 30 mmol), 2-chloroethanol (6.03 ml, 90 mmol) and triphenylphosphine (23.6 g, 90 mmol) in tetrahydrofuran is treated with diethyl azodicarboxylate (14.1 ml, 90 mmol) under nitrogen at room temperature, stirred for 2 hr at room temperature and concentrated in vacuo to give a residue. Cooled diethyl ether is added to the residue and the solid triphenylphosphine oxide is precipitated and removed by filtration. The filtrate is concentrated and purified by flash chromatography (silica gel, EtOAc/hexane: 1.5/8.5) to give an oil. After trituration with Et₂O/hexane (1/10), the title compound is obtained as a white solid, 4.8 g (82%) mp 60° C., identified by NMR and mass spectral analyses.

EXAMPLE 2

Preparation of 4-(2-Chloroethoxy)-1-(Phenylsulfonyl)-1H-Indole

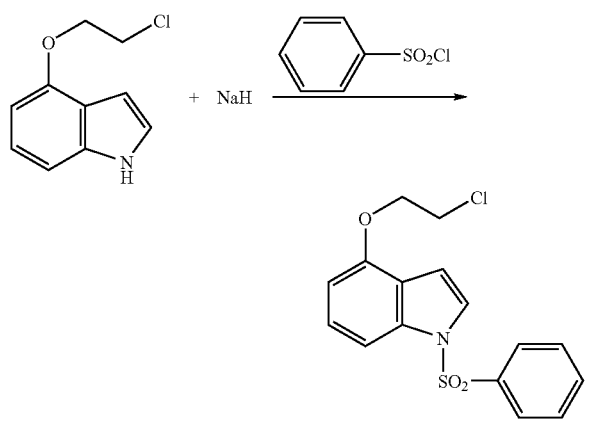

A stirred solution of 4-(2-chloroethoxy)-1H-indole (3.4 g, 17.4 mmol) in tetrahydrofuran is treated with sodium hydride (60% in mineral oil, 1.04 g, 26.1 mmol) under nitrogen at room temperature, stirred for 30 minutes, treated with benzenesulfonyl chloride (3.4 mL, 26.1 mmol) stirred at room temperature overnight and treated with saturated NaHCO₃ and EtOAc. The resultant phases are separated. The aqueous phase is extracted with EtOAc and the combined organic phase is washed sequentially with H₂O and saturated NaCl, dried over MgSO₄ and concentrated in vacuo to give a residue. The residue is purified by flash chromatography (silica gel, EtOAc/hexane: 2/8) to give the title compound as an off-white solid, 4.94 g (86%), mp 85-87° C., identified by NMR and mass spectral analyses.

EXAMPLE 3

Preparation of 2-{[1-(Phenylsulfonyl)-1H-Indole-4-yl]oxy}ethylazide

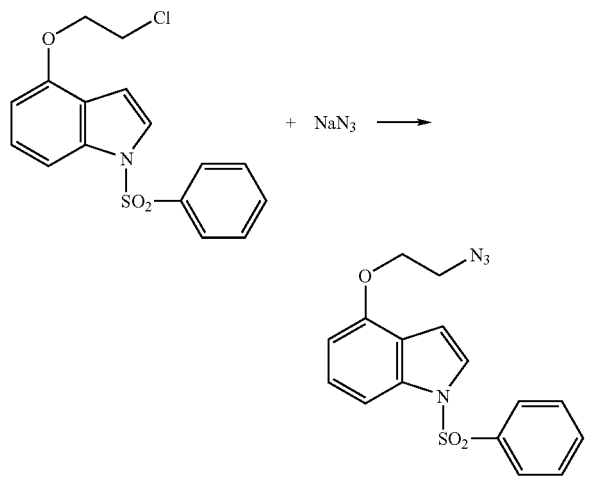

A suspension of 4-(2-chloroethoxy)-1-(phenylsulfonyl)-1H-indole (3.35 g, 10 mmol) and sodium azide (1.95 g, 30 mmol) in anhydrous dimethylformamide is stirred under nitrogen for 20 hr at 60° C., poured into water and extracted with diethyl ether. The extracts are combined, washed sequentially with 1N HCl, H₂O and saturated NaCl, dried over MgSO₄ and concentrated in vacuo to afford the title product as an off-white solid, 3.3 g (96%), identified by NMR and mass spectral analyses.

EXAMPLE 4

Preparation of 2-{[1-(Phenylsulfonyl)-1H-indole-4-yl]oxy}ethylamine

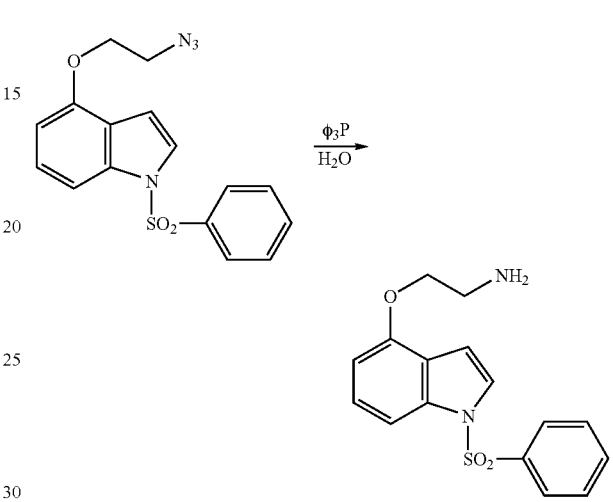

A mixture of 2-{[1-(phenylsulfonyl)-1H-indole-4-yl]oxy}ethylazide (3.3 g, 9.6 mmol) and triphenylphosphine (3.67 g, 14 mmol) in tetrahydrofuran and water is stirred under nitrogen for 24 hr at room temperature and filtered. The filtrate is concentrated in vacuo and the resultant residue is purified by flash chromatography (silica gel, EtOAc/MeOH/NH₄OH: 8.5/1.5/0.05) to afford the title compound as an off-white solid, 2.54 g (80%), mp 71-73° C., identified by NMR and mass spectral analyses.

EXAMPLE 5

Preparation of 2-{[1-(Phenylsulfonyl)-1H-indole-4-yl]oxy}ethylamine hydrochloride

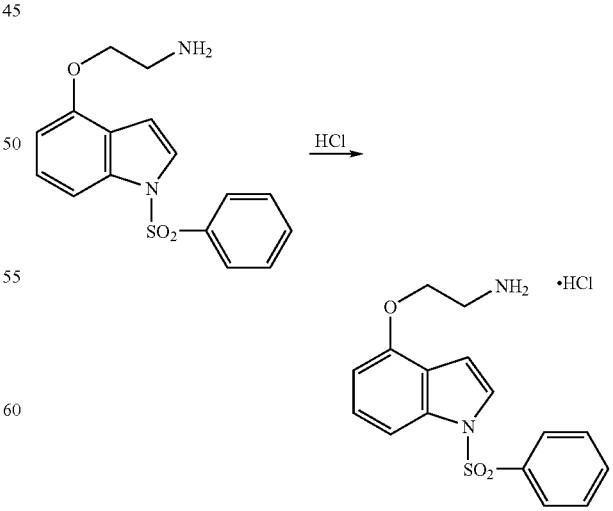

A solution of 2-{[1-(phenylsulfonyl)-1H-indole-4-yl]oxy}ethylamine (0.20 g, 0.63 mmol) in ethyl acetate is treated with HCl in diethyl ether (1M, 0.7 ml) and filtered. The filtercake is dried in vacuo to afford the title product as a pink solid, 0.21 g, mp 198-200° C., identified by NMR and mass spectral analyses.

EXAMPLE 6

Preparation of N-(2{[1-(Phenylsulfonyl)-1H-indol-4-yl]oxy}ethyl)tetrahydro-2H-pyran-4-amine hydrochloride

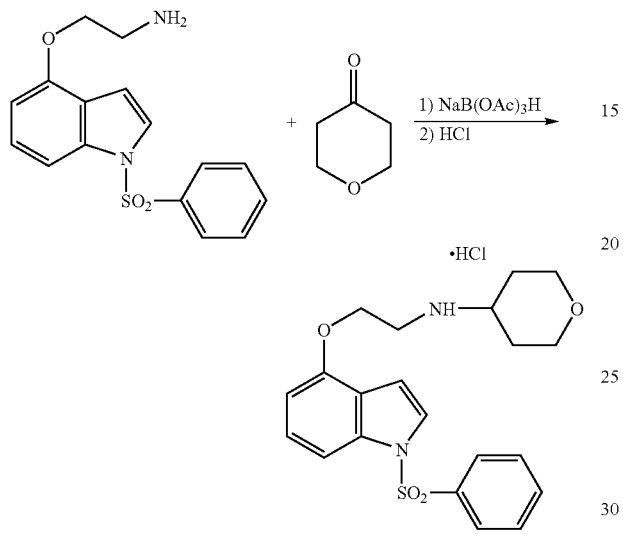

A mixture of 2-{[1-(phenylsulfonyl)-1H-indole-4-yl] oxy}ethylamine (0.316 g, 1.0 mmol), tetrahydro-4H-pyran-4-one (0.09 ml, 1.00 mmol) and sodium triacetoxyborohydride (0.312 g, 1.4 mmol) in 1,2-dichloroethane is treated with acetic acid (0.06 ml) at room temperature, stirred under nitrogen for 18 hr, quenched with concentrated aqueous NH$_4$OH and diluted with methylene chloride and water. The aqueous layer is separated and extracted with methylene chloride. The organic layer and extracts are combined, washed with saturated NaCl, dried over Na$_2$SO$_4$, and concentrated in vacuo. The resultant residue is purified by flash chromatography (silica gel, EtOAc/MeOH/NH$_4$OH: 9/1/0.05) to afford the free amine of the title product as a clear oil, 0.36 g (90%).

The HCl salt is prepared in HCl and ethyl acetate to give the title product as an off-white solid, mp 229-230° C., identified by NMR and mass spectral analyses.

EXAMPLES 7a AND 7b

Preparation of (a) N,N-Bis(3-methoxybenzyl)-N-(2-{[1-(phenylsulfonyl)-1H-indol-4-yl]oxy}ethylamine and (b) N-(3-methoxybenzyl)-N-(2-{[1-(phenylsulfonyl)-1H-indol-4-yl]oxy}ethylamine hydrochloride

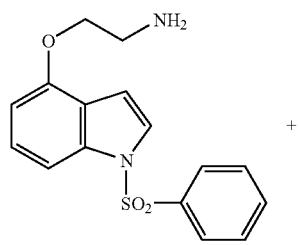

+

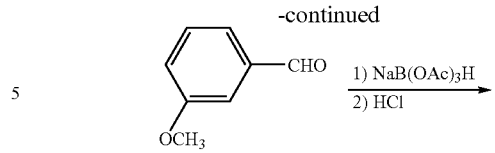

-continued

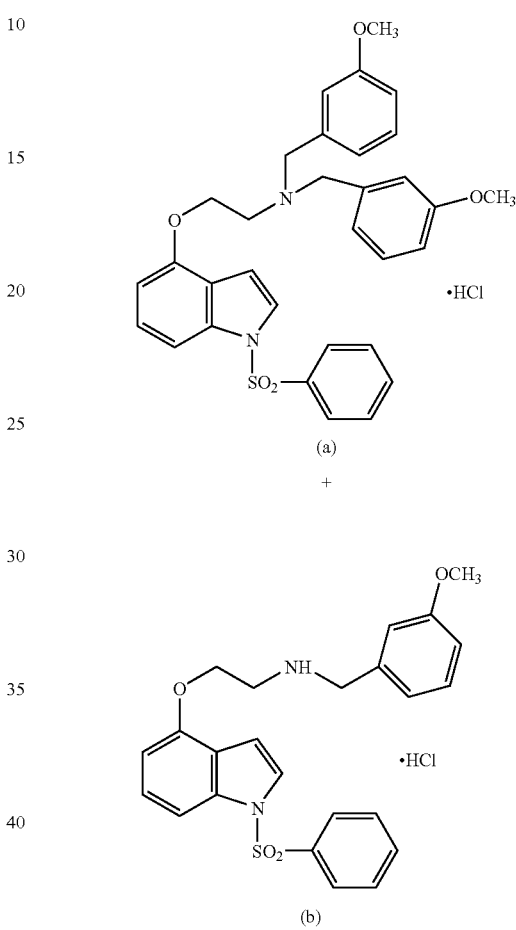

A mixture of 2-{[1-(phenylsulfonyl)-1H-indole-4-yl] oxy}ethylamine (0.316 g, 1.0 mmol), m-anisaldehyde (0.12 ml, 1.0 mmol) and sodium triacetoxyborohydride (0.312 g, 1.4 mmol) in 1,2-dichloroethane is treated with acetic acid (0.06 ml) at room temperature, stirred under nitrogen at room temperature for 18 hr, quenched with concentrated aqueous NH$_4$OH and diluted with methylene chloride and water. The aqueous layer is separated and extracted with methylene chloride. The organic layer and extracts are combined and washed with saturated NaCl dried over Na$_2$SO$_4$ and concentrated in vacuo to give a residue. The residue is purified by flash chromatography (silica gel, EtOAc/MeOH/NH$_4$OH: 9.5/0.5/0.05) to afford the free amine of 7a, 0.20 g (36%) as a clear oil and the free amine of 7b, 0.135 g (31%) as a clear oil.

The HCl salt of 7a is prepared in ethyl acetate and anhydrous HCl in ether to give the 7a title product as a white solid, mp 194-196° C., identified by NMR and mass spectral analyses.

The HCl salt of 7b is prepared in ethyl acetate and anhydrous HCl in ether to give the 7b title product as a white solid, mp 189-190° C., identified by NMR and mass spectral analyses.

EXAMPLE 8

Preparation of N,N-Dimethyl-N-(2-{[1-phenylsulfonyl)-1H-indol-4-yl]oxy}ethylamine hydrochloride

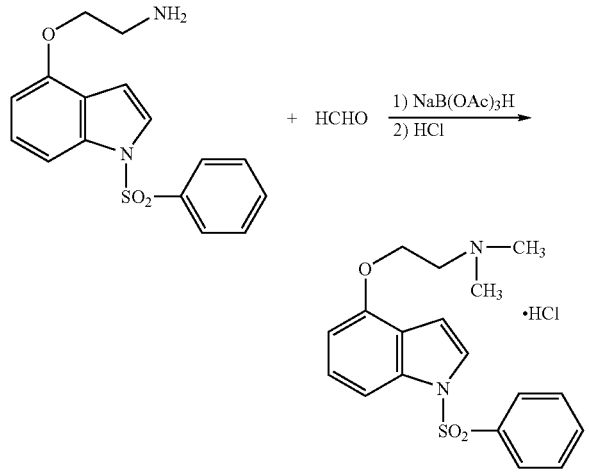

A mixture of 2-{[1-(phenylsulfonyl)-1H-indole-4-yl]oxy}ethylamine (0.316 g,1.0 mmol), formaldehyde (0.16 ml, 2.0 mmol) and sodium triacetoxyborohydride (0.446 g, 2.0 mmol) in 1,2-dichloroethane is stirred under nitrogen at room temperature for 48 hr, quenched with concentrated aqueous NH₄OH and diluted with methylene chloride. The aqueous layer is separated and extracted with methylene chloride. The organic layer and extracts are combined, washed with saturated NaCl, dried over Na₂SO₄ and concentrated in vacuo. The resultant residue is purified by flash chromatography (silica gel, EtOAc/MeOH/NH₄OH: 9.5/0.5/0.03) to afford the free amine as a white solid, 0.215 g (36%).

The HCl salt is prepared in ethyl acetate and anhydrous HCl in ether to give the title product as a white solid, mp 140-142° C., identified by NMR and mass spectral analyses.

EXAMPLE 9

Preparation of 4-(2-Morpholin-4-ylethoxy)-1-(phenyl-sulfonyl)-1H-indole hydrochloride

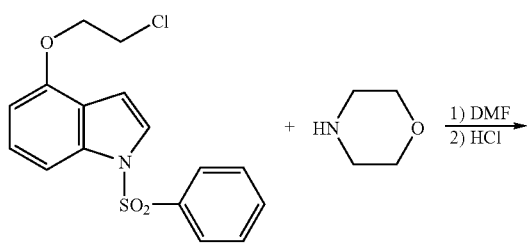

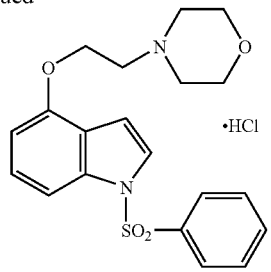

A mixture of 4-(2-chloroethoxy)-1-phenylsulfonyl-1H-indole (0.50 g, 1.5 mmol) and morpholine.(1.30 ml, 15 mmol) in dimethylformamide (DMF) is stirred under nitrogen at 80° C. for 18 hr, cooled to room temperature, quenched with water and extracted with diethyl ether. The combined ether extracts are washed with saturated sodium chloride, dried over MgSO₄, and concentrated in vacuo. The resultant residue is purified by flash chromatography (silica gel, EtOAc/MeOH/NH₄OH: 9.7/0.5/0.05) to afford the free amine as a white solid, 0.48 g (83%).

The HCl salt is prepared in ethyl acetate and HCl to afford the title product as a white solid, mp 140-142° C., identified by NMR and mass spectral analyses.

EXAMPLE 10

Preparation of 1-(Phenylsulfonyl)-4-(2-piperidin-1-ylethoxy)-1H-indole hydrochloride

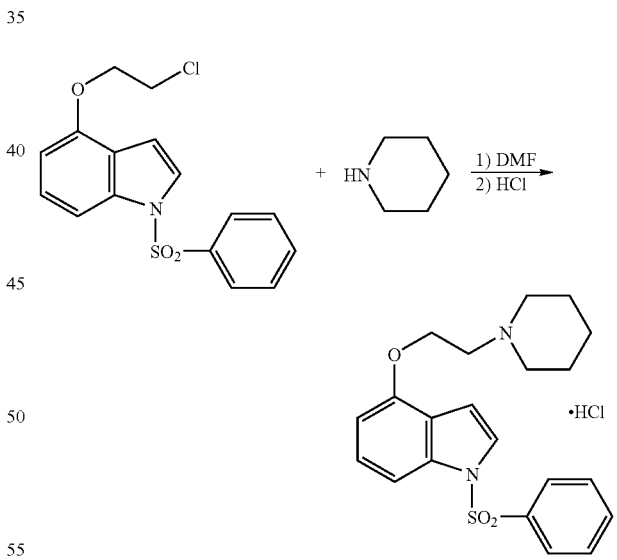

A mixture of 4-(2-chloroethoxy)-1-phenylsulfonyl-1H-indole (0.323 g, 1.0 mmol) and piperidine (0.99 ml, 10 mmol) in dimethylformamide (DMF) is stirred under nitrogen at 80° C. for 18 hr, cooled to room temperature, quenched with water and extracted with diethyl ether. The ether extracts are combined, washed with saturated sodium chloride, dried over MgSO₄ and concentrated in vacuo. The resultant residue is purified by flash chromatography (silica gel, EtOAc/MeOH/NH₄OH: 9.7/0.5/0.05) to afford the free amine as a light yellow oil 0.34 g (88%).

The HCl salt is prepared in ethyl acetate and HCl to give the title product as a light yellow solid, mp 131-133° C., identified by NMR and mass spectral analyses.

EXAMPLES 11-15

Preparation of 1-(Substituted-sulfonyl)-(2-piperidin-1-ylethoxy)-1H-indole Derivatives

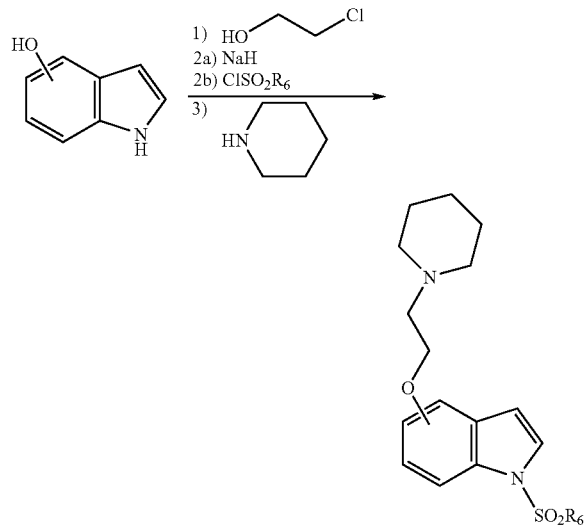

Using essentially the same procedures described in Examples 1, 2 and 10 and employing the appropriate hydroxyindole substrate and sulfonyl chloride reagent, the compounds shown in Table I are obtained and identified by NMR and mass spectral analyses.

TABLE I

| Ex. No. | Piperidinyl-ethoxy Ring Position | $R_6$ | mp ° C. |
|---|---|---|---|
| 11 | 5 | 5-chlorothien-2-yl | 222-224 |
| 12 | 5 | 4,5-dichlorothien-2-yl | 222-224 |
| 13 | 5 | 6-chloroimidazo[2,1-b][1,3]thiazol-5-yl | 60(foams) |
| 14 | 5 | 5-chloro-3-methyl-1-benzothien-2-yl | gum |
| 15 | 4 | 5-chloro-3-methyl-1-benzothien-2-yl | 217-219 |

EXAMPLE 16

Preparation of 4-(2-Chloroethoxy)-1H-indazole

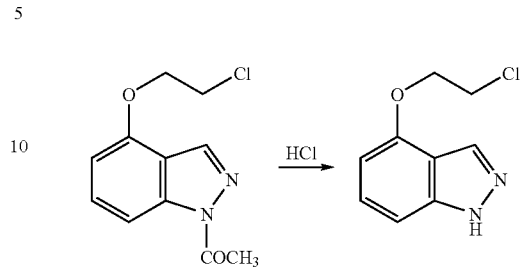

A stirred solution of 1-acetyl-4-(2-chloroethoxy)-indazole (1.50 g, 6.3 mmol) in methanol is treated with hydrochloric acid (6.3 ml, 1.0 M HCl in $Et_2O$, 6.3 mmol) at room temperature, heated at 65° C. under nitrogen for 18 hr, cooled to room temperature and concentrated in vacuo. The resultant residue is neutralized with 1N NaOH (6.0 ml) and diluted with $H_2O$ and ethyl acetate. The phases are separated and the aqueous phase is extracted with ethyl acetate. The combined organic phases are washed with water and saturated NaCl, dried over $Na_2SO_4$ and concentrated in vacuo to afford the title product (1.2 g) as a yellow solid, identified by NMR and mass spectral analyses.

EXAMPLE 17

Preparation of 4-(2-Chloroethoxy)-1-(phenylsulfonyl)-1H-indazole

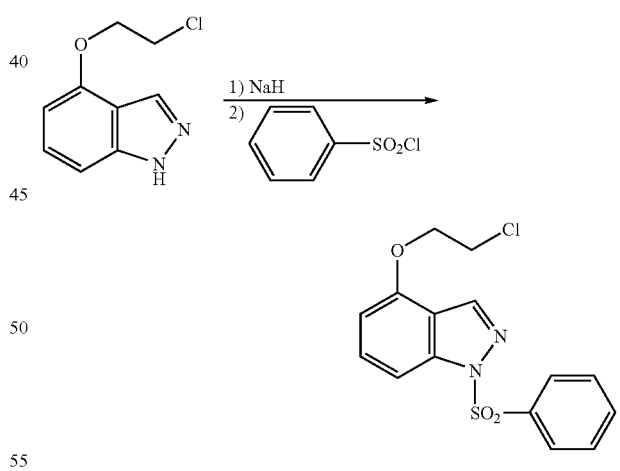

A stirred solution of 4-(2-chloroethoxy)-1H-indazole (1.1 g, 5.59 mmol) in tetrahydrofuran is treated with NaH (0.335 g, 60% in mineral oil, 8.39 mmol) under nitrogen at room temperature, stirred for 30 minutes, treated with benzenesulfonyl chloride (0.86 ml, 6.71 mmol), stirred at room temperature for 18 hr, quenched with water and diluted with ethyl acetate. The phases are separated and the organic phase is washed with water and brine, dried over $MgSO_4$ and concentrated in vacuo. The resultant residue is purified by flash chromatography (silica gel, EtOAc/hexane: 3/7) to give the desired product as a white solid, 1.75 g (93%), mp 102-104° C., identified by NMR and mass spectral analyses.

EXAMPLE 18

Preparation of 1-Phenylsulfonyl)-4-[-piperidinyl) ethoxyl]-1H-indazole hydrochloride

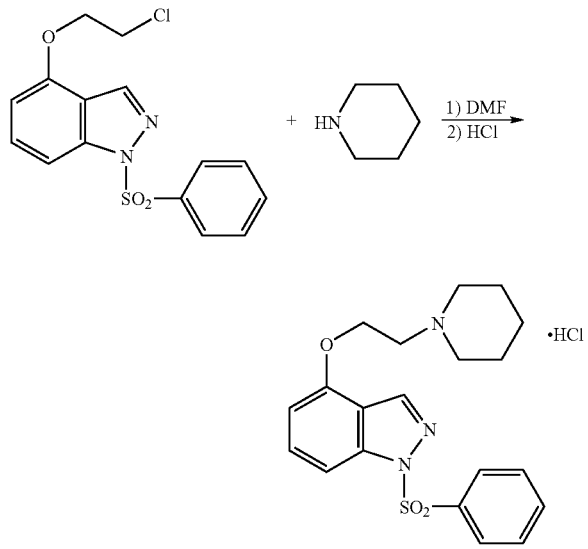

A mixture of 4-(2-chloroethoxy)-1-(phenylsulfonyl)-1H-indazole (0.337 g, 1.0 mmol) and piperidine (0.20 ml, 2.0 mmol) in N,N-dimethylformamide (DMF)is stirred under nitrogen at 80° C. for 18 hr, cooled, quenched with ice-water and diluted with ethyl acetate. The phases are separated. The aqueous phase is extracted with ethyl acetate. The organic phases are combined, washed with water and saturated NaCl, dried over MgSO$_4$ and concentrated in vacuo to give a yellow oil residue. The residue is dissolved in ethyl acetate, treated with 1M HCl (1 ml, 1M HCl in Et$_2$O) and filtered. The filtercake is dried under vacuum to afford the title product as an off-white solid, 354 mg, mp 87-89° C., identified by NMR and mass spectral analyses.

EXAMPLE 19

Preparation of 2-{[1-Phenylsulfonyl)-1H-indazol-4-yl]oxy}ethylamine hydrochloride

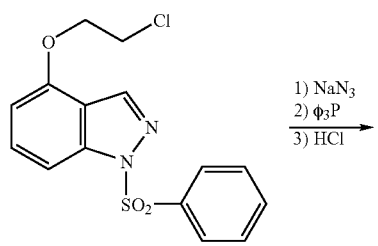

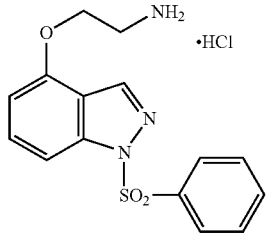

A suspension of 4-(2-chloroethoxy)-1-(phenylsulfonyl)-1H-indazole (0.66 g, 1.96 mmol) and sodium azide (0.382 g, 5.87 mmol) in N,N-dimethyl-formamide is stirred under nitrogen at 60° C. for 24 hr, cooled, quenched with 1N HCl and extracted with ethyl acetate. The combined extracts are washed with water and saturated NaCl, dried over Na$_2$SO$_4$ and concentrated in vacuo to give a yellow solid residue. The residue is dissolved in tetrahydrofuran, treated with triphenyl-phosphine (0.771 g, 2.94 mmol) and water, stirred at room temperature for 18 hr and concentrated in vacuo. The resultant residue is purified by flash chromatography (silica gel, EtOAc/2M NH3 in MeOH: 90/10) to give the free amine (0.41 g) as a gum. The gum is dissolved in ethyl acetate and treated with anhydrous HCl in ether. The reaction mixture is filtered and the filtercake is air-dried to give the title product as a white solid, mp 201-203° C., identified by NMR and mass spectral analyses.

EXAMPLES 20-26

Preparation of 1-(Substituted-sulfonyl)-4-[2-(1-piperidinyl)-ethoxyl]-1H-indazole Derivatives

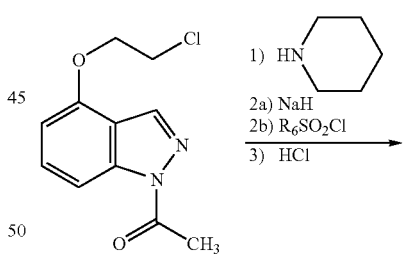

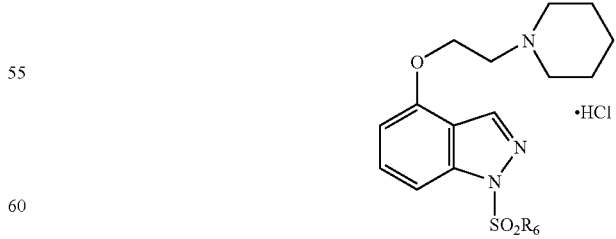

Using essentially the same procedures described in Examples 16, 17 and 18 and employing the appropriate sulfonyl chloride, the compounds shown in Table II are obtained and identified by NMR and mass spectral analyses.

TABLE II

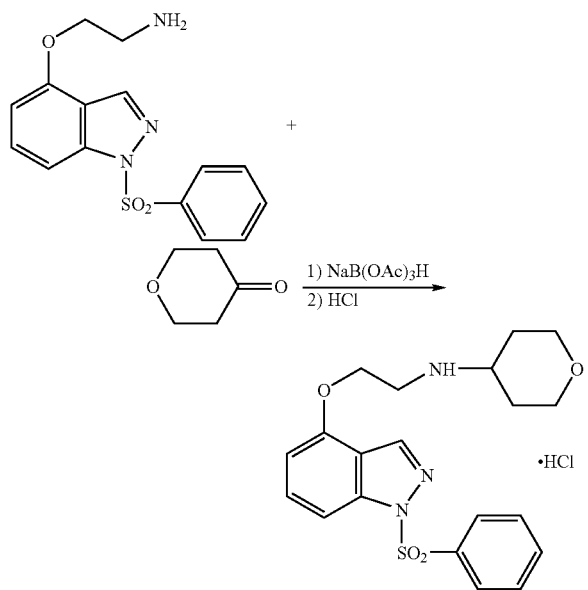

| Ex. No. | R₆ | mp °C. |
|---|---|---|
| 20 | 4-nitrophenyl | 117-119 |
| 21 | 4-fluorophenyl | 122 (dec) |
| 22 | 6-chloroimidazo[2,1-b][1,3]thiazol-5-yl | 88-90 |
| 23 | 4,5-dichlorothien-2-yl | 214-216 |
| 24 | 5-chlorothien-2-yl | 187-189 |
| 25 | thien-2-yl | 172-175 |
| 26 | 5-chloro-3-methyl-1-benzothien-2-yl | 216-218 |

EXAMPLE 27

Preparation of N-(2-{[1-Phenylsulfonyl)-1H-indazol-4yl]oxy}ethyl)tetrahydro-2H-pyran-4-amine

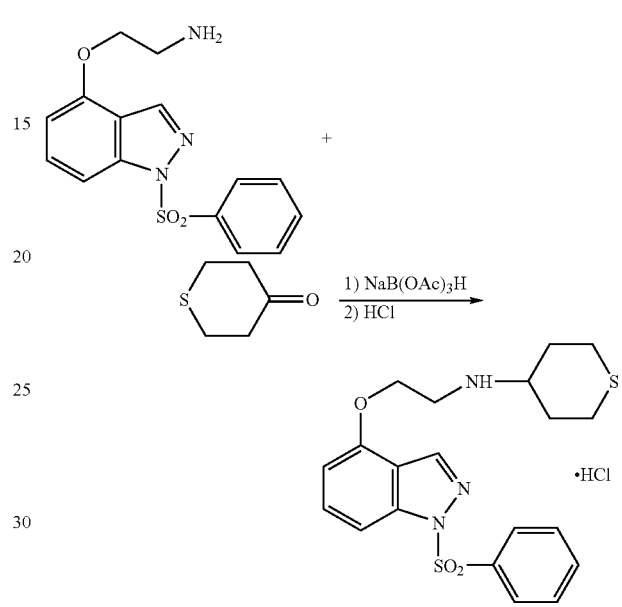

A suspension of 2-{[1-(phenylsulfonyl)-1H-indazol-4-yl]oxy}ethylamine (0.10 g, 0.31 mmol), tetrahydro-4H-pyran-4-one (0.03 ml, 0.31 mmol) and sodium triacetoxyborohydride (0.097 g, 0.43 mmol) in 1,2-dichloroethane is treated with acetic acid (0.03 ml) at room temperature, allowed to stir under nitrogen at room temperature for 18 hr, quenched with 1 N NaOH (2 ml) and diluted with water and a 4:1 mixture of methylene chloride:isopropanol. The phases are separated and the aqueous phase is further extracted with a 4:1 mixture of methylene chloride:isopropanol. The organic phases are combined, washed with water and brine, dried over Na₂SO₄ and concentrated in vacuo. The resultant residue is dissolved in a 4:1 mixture of ethyl acetate:isopropanol, treated with anhydrous HCl in ether and filtered to obtain the title product as a white solid, mp 173-175° C., identified by NMR and mass spectral analyses.

EXAMPLE 28

Preparation of N-(2-{[1-Phenylsulfonyl)-1H-indazol-4-yl]oxy}ethyl)tetrahydro-2H-thiopyran-4-amine hydrochloride

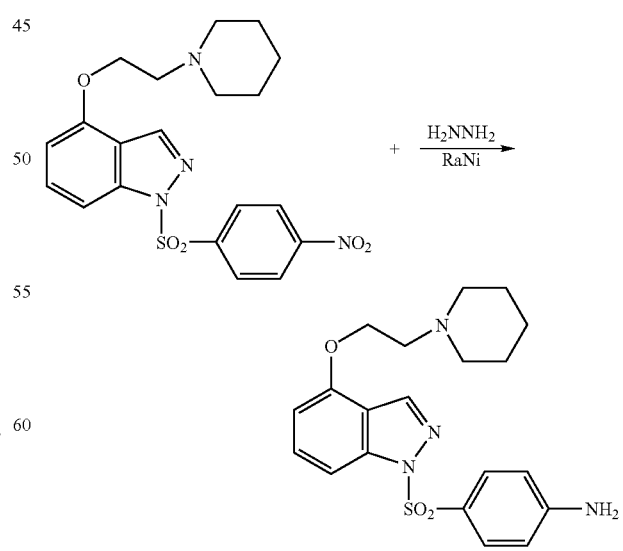

Using essentially the same procedures described in Example 17 and substituting tetrahydrothiopyran-4-one as the reactant, the title product is obtained as a white solid, mp 182-184° C., identified by NMR and mass spectral analyses.

EXAMPLE 29

Preparation of 4-({4-[2-(1-Piperidinyl)ethoxy]-1H-indazol-1-yl}sulfonyl)aniline

A stirred solution of 1-[(4-nitrophenyl)sulfonyl]-4-[2-(1-piperidinyl)ethoxy]1H-indazole (0.39 g, 0.91 mol) in methanol is treated with Raney Nickel followed by hydrazine (0.2 ml, 6.3 mmol), stirred at 0° C. for 2 hr and decanted. The catalyst is washed with a methanol:

methylene chloride 3:7 mixture. The washes and supernatant are combined and concentrated in vacuo. The resultant residue is purified by flash chromatography (silicagel, EtOAc/ 2M $NH_3$ in methanol 8:2) to give the title product as a white solid, 0.15 g, mp 149-150° C. (dec), identified by NMR and mass spectral analyses.

EXAMPLE 30

Comparative Evaluation of 5-HT6 Binding Affinity of Test Compounds

The affinity of test compounds for the serotonin 5-HT6 receptor is evaluated in the following manner. Cultured Hela cells expressing human cloned 5-HT6 receptors are harvested and centrifuged at low speed (1,000×g) for 10.0 min to remove the culture media. The harvested cells are suspended in half volume of fresh physiological phosphate buffered saline solution and recentrifuged at the same speed. This operation is repeated. The collected cells are then homogenized in ten volumes of 50 mM Tris.HCl (pH 7.4) and 0.5 mM EDTA. The homogenate is centrifuged at 40,000×g for 30.0 min and the precipitate is collected. The obtained pellet is resuspended in 10 volumes of Tris.HCl buffer and recentrifuged at the same speed. The final pellet is suspended in a small volume of Tris.HCl buffer and the tissue protein content is determined in aliquots of 10-25 μl volumes. Bovine Serum Albumin is used as the standard in the protein determination according to the method described in Lowry et al., *J. Biol. Chem.*, 193:265 (1951). The volume of the suspended cell membranes is adjusted to give a tissue protein concentration of 1.0 mg/ml of suspension. The prepared membrane suspension (10 times concentrated) is aliquoted in 1.0 ml volumes and stored at −70° C. until used in subsequent binding experiments.

Binding experiments are performed in a 96 well microtiter plate format, in a total volume of 200 μl. To each well is added the following mixture: 80.0 μl of incubation buffer made in 50 mM Tris.HCl buffer (pH 7.4) containing 10.0 mM $MgCl_2$ and 0.5 mM EDTA and 20 μl of [$^3$H]-LSD (S.A., 86.0 Ci/mmol, available from Amersham Life Science), 3.0 nM. The dissociation constant, $K_D$ of the [$^3$H]LSD at the human serotonin 5-HT6 receptor is 2.9 nM, as determined by saturation binding with increasing concentrations of [$^3$H]LSD. The reaction is initiated by the final addition of 100.0 μl of tissue suspension. Nonspecific binding is measured in the presence of 10.0 μM methiothepin. The test compounds are added in 20.0 μl volume.

The reaction is allowed to proceed in the dark for 120 min at room temperature, at which time, the bound ligand-receptor complex is filtered off on a 96 well unifilter with a Packard Filtermate® 196Harvester. The bound complex caught on the filter disk is allowed to air dry and the radioactivity is measured in a Packard TopCount® equipped with six photomultiplier detectors, after the addition of 40.0 μl Microscint®-20 scintillant to each shallow well. The unifilter plate is heat-sealed and counted in a PackardTopCount® with a tritium efficiency of 31.0%.

Specific binding to the 5-HT6 receptor is defined as the total radioactivity bound less the amount bound in the presence of 10.0 μM unlabeled methiothepin. Binding in the presence of varying concentrations of test compound is expressed as a percentage of specific binding in the absence of test compound. The results are plotted a log % bound versus log concentration of test compound. Nonlinear regression analysis of data points with a computer assisted program Prism® yielded both the $IC_{50}$ and the $K_i$ values of test compounds with 95% confidence limits. A linear regression line of data points is plotted, from which the $IC_{50}$ value is determined and the $K_i$ value is determined based upon the following equation:

$$K_i = IC_{50}/(1+L/K_D)$$

where L is the concentration of the radioactive ligand used and $K_D$ is the dissociation constant of the ligand for the receptor, both expressed in nM.

Using this assay, the following Ki values are determined and compared to those values obtained by representative compounds known to demonstrate binding to the 5-HT6 receptor. The data are shown in Table III, below.

TABLE III

| Test Compound (Ex. No.) | 5-HT6 Binding Ki (nM) |
|---|---|
| 5 | 2 |
| 6 | 6 |
| 7a | 94% @ 1 μM* |
| 7b | 95% @ 1 μM* |
| 8 | 4 |
| 9 | 92% @ 1 μM* |
| 10 | 7 |
| 11 | 51% @ 1 μM* |
| 12 | 65% @ 1 μM* |
| 13 | 22 |
| 14 | 65% @ 1 μM* |
| 15 | 71 |
| 18 | 2 |
| 19 | 1 |
| 20 | 76% @ 1 μM* |
| 21 | 19 |
| 22 | 2 |
| 23 | 18 |
| 24 | 12 |
| 25 | 8 |
| 26 | 53 |
| 27 | 6 |
| 28 | 11 |
| 29 | 1 |
| Comparative Examples | |
| Clozapine | 6.0 |
| Loxapine | 41.4 |
| Bromocriptine | 23.0 |
| Methiothepin | 8.3 |
| Mianserin | 44.2 |
| Olanzepine | 19.5 |

*% inhibition at 1 μM concentration

As can be seen from the results set forth above, the compounds of the present invention have a high degree of affinity for the serotonin 5-HT6 receptor.

What is claimed is:

1. A compound of formula I

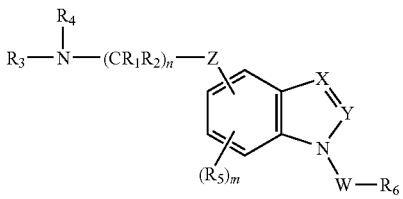

wherein
W is $SO_2$, CO, CONH, CSNH or $CH_2$;
X is $CR_7$ or N;
Y is $CR_8$;
Z is O, $SO_p$ or $NR_9$;
$R_1$ and $R_2$ are each independently H or $C_1$-$C_6$alkyl;
n is an integer of 2, 3 or 4;
$R_3$ and $R_4$ are taken together with the atom to which they are attached to form an optionally substituted 3- to 6-membered ring optionally containing an additional heteroatom selected from O, N or S;
$R_5$ is H, halogen, CN, $OR_{13}$, $CO_2R_{14}$, $CONR_{15}R_{16}$, $CNR_{17}NR_{18}R_{19}$, $SO_2NR_{20}R_{21}$, $SO_qR_{22}$ or a $C_1$-$C_6$alkyl, $C_2$-$C_6$alkenyl, $C_2$-$C_6$alkynyl, $C_3$-$C_6$cycloalkyl, cycloheteroalkyl, phenyl or heteroaryl group each optionally substituted;
m is an integer of 1, 2 or 3;
p and q are each independently 0 or an integer of 1 or 2;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
$R_7$ and $R_8$ are each independently H, halogen or a $C_1$-$C_6$ alkyl, aryl, heteroaryl or $C_1$-$C_6$alkoxy group each optionally substituted;
$R_9$ is H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{15}$, $R_{16}$, $R_{17}$, $R_{18}$ and $R_{19}$ are each independently H or $C_1$-$C_4$alkyl;
$R_{13}$ is H, $COR_{23}$ or a $C_1$-$C_6$alkyl, $C_2$-$C_6$alkenyl, $C_2$-$C_6$alkynyl, aryl or heteroaryl group each optionally substituted;
$R_{14}$ is H or a $C_1$-$C_6$alkyl, aryl or heteroaryl group each optionally substituted;
$R_{20}$ and $R_{21}$ are each independently H or a $C_1$-$C_6$alkyl, aryl or heteroaryl group each optionally substituted; and
$R_{22}$ and $R_{23}$ are each independently an optionally substituted $C_1$-$C_6$alkyl, aryl or heteroaryl group; or
a pharmaceutically acceptable salt thereof.

2. The compound according to claim 1 wherein W is $SO_2$.

3. The compound according to claim 1 wherein Z is O.

4. The compound according to claim 1 wherein n is 2.

5. The compound according to claim 1 wherein $R_6$ is an optionally substituted thienyl or imidazothiazolyl group.

6. The compound according to claim 1 wherein X is $CR_7$ and $R_5$ and $R_7$ are H.

7. The compound according to claim 2 wherein $R_1$ and $R_2$ are H; Z is O; and n is 2.

8. The compound according to claim 6 wherein W is $SO_2$; Z is O; and $R_3$ and $R_4$ are taken together with the atom to which they are attached to form a 5- or 6-membered ring optionally containing one oxygen atom.

9. The compound according to claim 6 selected from the group consisting of:
1-[(5-chlorothien-2-yl)sulfonyl]-5-[2-(piperidin-1-yl) ethoxy]-1H-indole;
1-[(4, 5-dichlorothien-2-yl)sulfonyl]-5-[2-(piperidin-1-yl) ethoxy]-1H-indole;
1-[(6-chloroimidazo[2,1-b][1,3]thiazol-5-yl)sulfonyl]-5-[2-(piperidin-1-yl)ethoxy]-1H-indole;
1-[(5-chloro-3-methyl-1-benzothien-2-yl)sulfonyl]-5-[2-(piperidin-1-yl)ethoxy]-1H-indole;
1-[(5-chloro-3-methyl-1-benzothien-2-yl)sulfonyl]-4-[2-(piperidin-1-yl)ethoxy]-1H-indole; and
a pharmaceutically acceptable salt thereof.

10. A pharmaceutical composition which comprises a pharmaceutically acceptable carrier and an effective amount of a compound of formula I

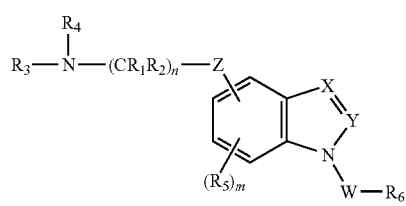

wherein
W is $SO_2$, CO, CONH, CSNH or $CH_2$;
X is $CR_7$ or N;
Y is $CR_8$;
Z is O, $SO_p$ or $NR_9$;
$R_1$ and $R_2$ are each independently H or $C_1$-$C_6$alkyl;
n is an integer of 2, 3 or 4;
$R_3$ and $R_4$ are taken together with the atom to which they are attached to form an optionally substituted 3- to 6-membered ring optionally containing an additional heteroatom selected from O, N or S;
$R_5$ is H, halogen, CN, $OR_{13}$, $CO_2R_{14}$, $CONR_{15}R_{16}$, $CNR_{17}NR_{18}R_{19}$, $SO_2NR_{20}R_{21}$, $SO_qR_{22}$ or a $C_1$-$C_6$alkyl, $C_2$-$C_6$alkenyl, $C_2$-$C_6$alkynyl, $C_3$-$C_6$cycloalkyl, cycloheteroalkyl, phenyl or heteroaryl group each optionally substituted;
m is an integer of 1, 2 or 3;
p and q are each independently 0 or an integer of 1 or 2;
$R_6$ is an optionally substituted heteroaryl group or an optionally substituted 8- to 13-membered bicyclic or tricyclic ring system having a N atom at the bridgehead and optionally containing 1, 2 or 3 additional heteroatoms selected from N, O or S;
$R_7$ and $R_8$ are each independently H, halogen or a $C_1$-$C_6$ alkyl, aryl, heteroaryl or $C_1$-$C_6$alkoxy group each optionally substituted;
$R_9$ is H or a $C_1$-$C_6$alkyl, $C_2$-$C_6$alkenyl, $C_2$-$C_6$alkynyl, $C_3$-$C_6$cycloalkyl, cycloheteroalkyl, aryl or heteroaryl group each optionally substituted;
$R_{15}$, $R_{16}$, $R_{17}$, $R_{18}$ and $R_{19}$ are each independently H or $C_1$-$C_4$alkyl;
$R_{13}$ is H, $COR_{23}$ or a $C_1$-$C_6$alkyl, $C_2$-$C_6$alkenyl, $C_2$-$C_6$alkynyl, aryl or heteroaryl group each optionally substituted;
$R_{14}$ is H or a $C_1$-$C_6$alkyl, aryl or heteroaryl group each optionally substituted;

R_{20} and R_{21}, are each independently H or a $C_1$-$C_6$ alkyl, aryl or heteroaryl group each optionally substituted; and R_{22} and R_{23} are each independently an optionally substituted $C_1$-$C_6$ alkyl, aryl or heteroaryl group; or a pharmaceutically acceptable salt thereof.

11. The composition according to claim 10 wherein W is $SO_2$; Z is O; and n is 2.

12. The composition according to claim 11 wherein $R_6$ is an optionally substituted thienyl or imidazothiazolyl group.

13. The composition according to claim 12 wherein X is $CR_7$ and $R_1$, $R_2$, $R_5$, and $R_7$ are H.

14. The composition according to claim 10 having a formula I compound selected from the group consisting of:

1-[(5-chlorothien-2-yl)sulfonyl]-5-[2-(piperidin-1-yl)ethoxy]-1H-indole;
1-[(4,5-dichlorothien-2-yl)sulfonyl]-5-[2-(piperidin-1-yl)ethoxy]-1H-indole;
1-[(6-chloroimidazo[2,1-b][1,3]thiazol-5-yl)sulfonyl]-5-[2-(piperidin-1-yl)ethoxy]-1H-indole;
1-[(5-chloro-3-methyl-1-benzothien-2-yl)sulfonyl]-5-[2-(piperidin-1-yl)ethoxy]-1H-indole;
1-[(5-chloro-3-methyl-1-benzothien-2-yl)sulfonyl]-4-[2-(piperidin-1-yl)ethoxy]-1H-indole; and a pharmaceutically acceptable salt thereof.

15. The compound according to claim 1 of formula I

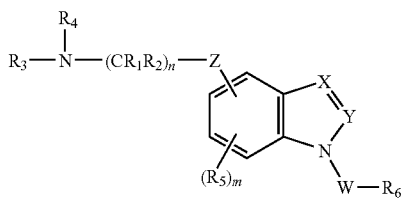

(I)

wherein
W is $SO_2$;
X is $CR_7$ or N;
Y is $CR_8$;
Z is O;
$R_1$ and $R_2$ are each independently H or $C_1$-$C_6$ alkyl;
n is an integer of 2, 3 or 4;
$R_3$ and $R_4$ are taken together with the atom to which they are attached to form an optionally substituted 3-to 6-membered ring optionally containing an additional heteroatom selected from O, N or S;
$R_5$ is H, halogen, CN, $OR_{13}$, or a $C_1$-$C_6$ alkyl group optionally substituted with halo;
m is an integer of 1, 2 or 3;
$R_6$ is an optionally substituted heteroaryl group or an optionally substituted 8-to 13-membered bicyclic or tricyclic ring system having a N atom at the bridgehead and optionally containing 1, 2 or 3 additional heteroatoms selected from N, O or S;

$R_7$ and $R_8$ are each independently H, halogen or a $C_1$-$C_6$ alkyl optionally substituted with halo;
$R_{13}$ is H, $COR_{23}$ or a $C_1$-$C_6$ alkyl optionally substituted with halo;
$R_{23}$ is $C_1$-$C_6$ alkyl optionally substituted with halo; or
a pharmaceutically acceptable salt thereof.

16. The compound according to claim 15 of formula I

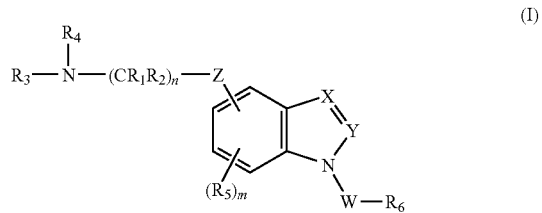

(I)

wherein
W is $SO_2$;
X is $CR_7$ or N;
Y is $CR_8$;
Z is O;
$R_1$ and $R_2$ are each independently H;
n is 2;
$R_3$ and $R_4$ are taken together with the atom to which they are attached to form an optionally substituted 3-to 6-membered ring optionally containing an additional heteroatom selected from O, N or S;
$R_5$ is H, halogen, —CN, —OH, —O($C_1$-$C_6$alkyl), or $C_1$-$C_6$alkyl;
m is 1;
$R_6$ is an optionally substituted heteroaryl group or an optionally substituted 8-to 13-membered bicyclic or tricyclic ring system having a N atom at the bridgehead and optionally containing 1, 2 or 3 additional heteroatoms selected from N, O or S;
$R_7$ and $R_8$ are each independently H, halogen or $C_1$-$C_6$ alkyl; or
a pharmaceutically acceptable salt thereof.

17. The compound according to claim 16 wherein X is $CR_7$.

18. The compound according to claim 16 wherein X is N.

19. A method for the treatment of schizophrenia or depression in a patient in need thereof which comprises providing to said patient a therapeutically effective amount of a compound of claim 1.

20. A method for the treatment of Alzheimer's disease or Parkinson's disease in a patient in need thereof which comprises providing to said patient a therapeutically effective amount of a compound of claim 1.

* * * * *